United States Patent [19]

Helixon

[11] 4,369,355
[45] Jan. 18, 1983

[54] LENS CASE AND HEATING UNIT

[75] Inventor: Michael L. Helixon, Fort Worth, Tex.

[73] Assignee: Alcon Laboratories, Inc., Fort Worth, Tex.

[21] Appl. No.: 170,709

[22] Filed: Jul. 21, 1980

[51] Int. Cl.³ .......................... H05B 3/06; A61L 2/04
[52] U.S. Cl. .................................. 219/521; 219/386; 219/401; 422/38; 422/301; 422/302; 422/307
[58] Field of Search .............. 422/307, 300, 301, 302, 422/28, 38; 219/386, 401, 521

[56] References Cited

U.S. PATENT DOCUMENTS

| | | | |
|---|---|---|---|
| D. 256,159 | 7/1980 | Thomas et al. | 422/243 X |
| 4,228,136 | 10/1980 | Thomas | 422/307 |
| 4,235,842 | 11/1980 | Thomas et al. | 422/307 X |
| 4,242,572 | 12/1980 | Thomas et al. | 422/300 X |
| 4,256,952 | 3/1981 | Thomas et al. | 422/307 X |
| 4,303,828 | 12/1981 | Thomas et al. | 219/521 |
| 4,307,289 | 12/1981 | Thomas et al. | 422/307 X |

Primary Examiner—Barry S. Richman
Attorney, Agent, or Firm—Fitch, Even, Tabin, Flannery & Welsh

[57] ABSTRACT

A contact lens bathing case, in which a pair of contact lenses is sealed with a cleaning and disinfectant solution, and a heating unit, for receiving and heating the filled case therein, cooperate to eliminate leakage problems, i.e. loss of solution, associated with improperly closed contact lens cases. The heating case includes a heating element and a movable lens case holder which is movable from an open position remote from the heating element to a closed position adjacent to the heating element whereat the solution and lenses may be heated. Closure prevention means prevent the holder which has received an improperly closed case from being moved to the closed position.

4 Claims, 15 Drawing Figures

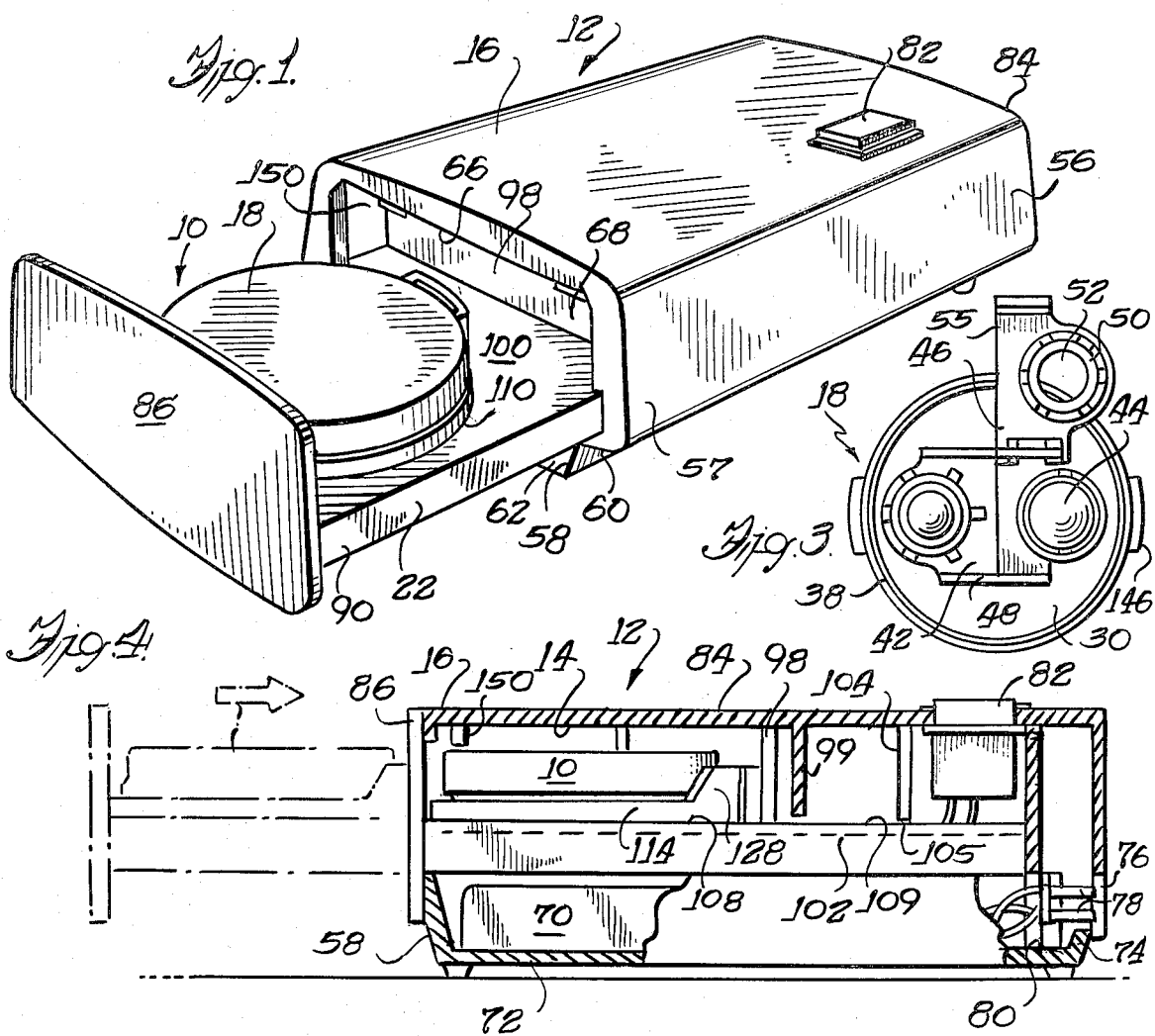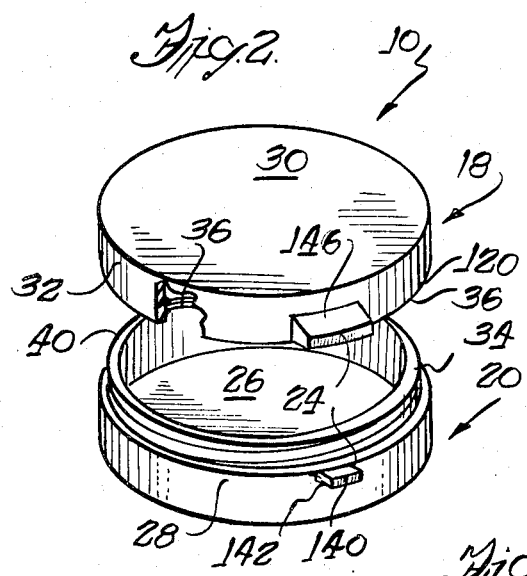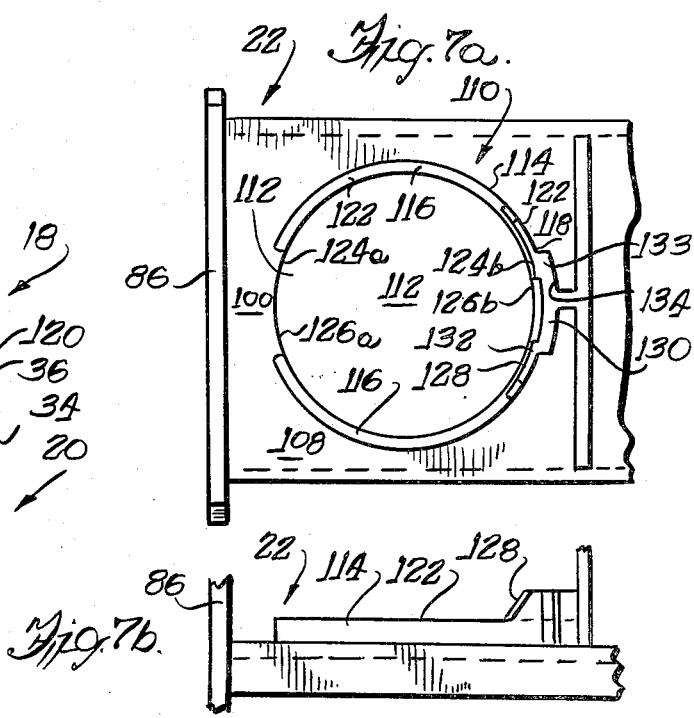

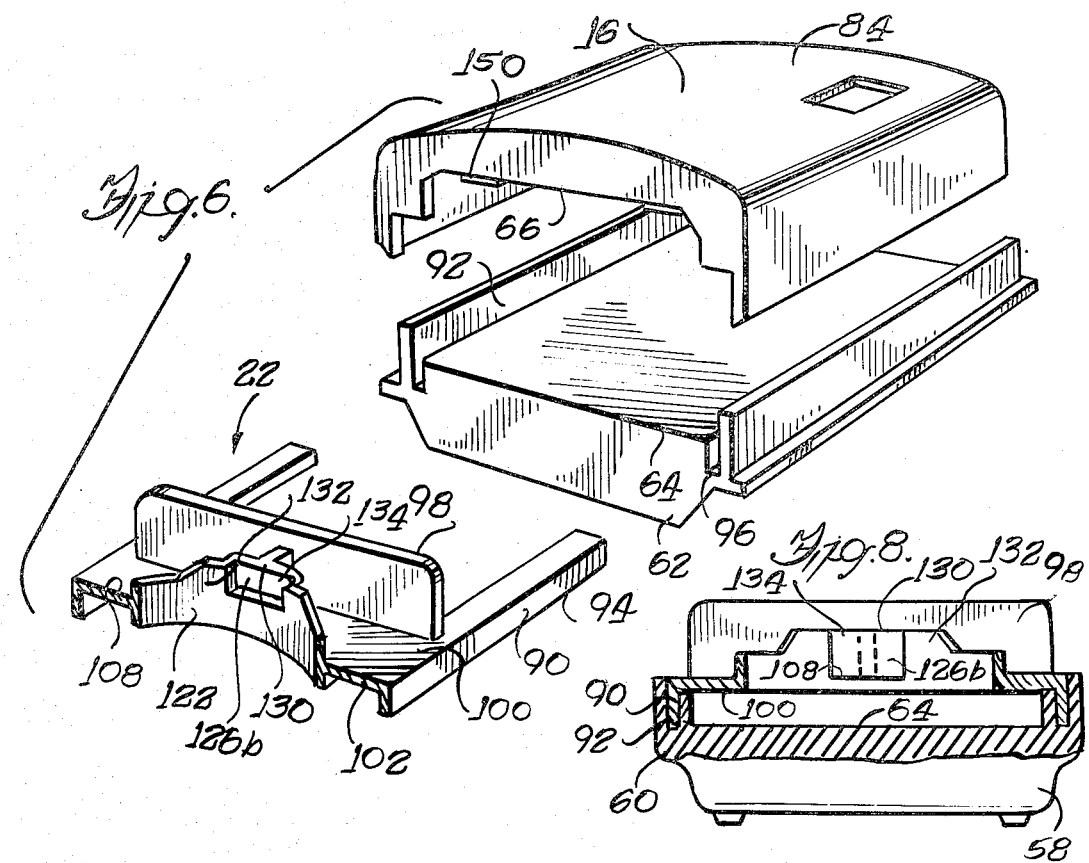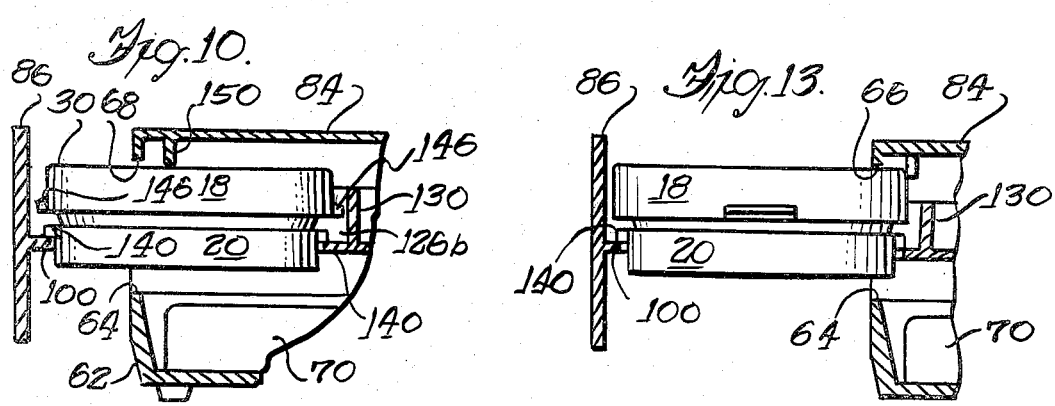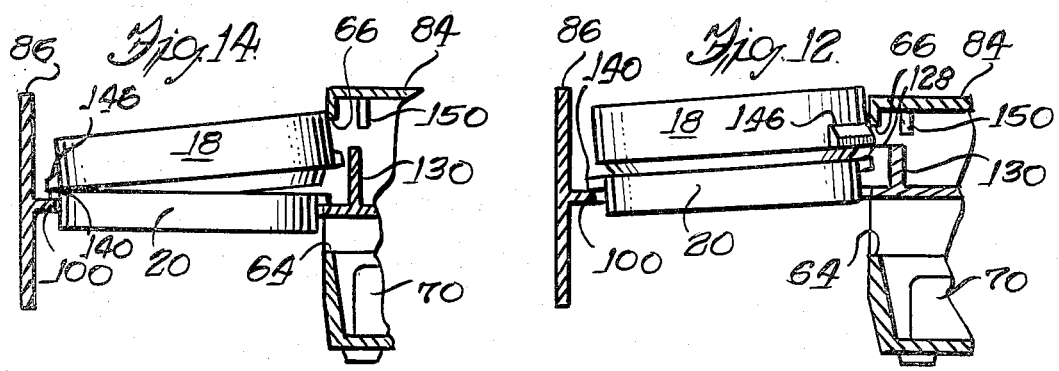

LENS CASE AND HEATING UNIT

The present invention relates to apparatus to heat a contact lens bathing solution.

In use, contact lenses will be contaminated with microorganisms from the eye as well as from the surroundings. Furthermore, contact lenses will become stained with protein deposits from the eye as well as dirt and grime from outside sources. In order not to cause eye infections, and to prevent the build-up of deposits which will permanently cloud the optical properties of the lenses, lenses should be disinfected and cleaned once every 24 hours. The cleaning ability of most contact lens cleaning solutions is enhanced if the solution is heated while the contact lens is bathed therein. Heating also has the effect of disinfecting since elevated temperatures kill many microorganisms. It is common, therefore, to heat the solution of contact lens cleaning solutions even to boiling.

It is particularly important to bathe soft contact lenses. Soft contact lenses, which provide comfort due to their ability to adapt to the shape of the eye, are manufactured from a polymer, such as polymethylmethacrylate, which is used in the hydrated state and cooperates with the tear fluid of the eye to achieve the proper optical properties. To prolong the life of soft lenses, the lenses should be bathed whenever they are not in the eye to maintain proper hydration of the polymer.

While one could simply heat or boil a contact lens bathing solution by placing a contact lens in a solution and placing the solution on a stove or other heating element, an inherent risk is that the solution will boil away. Boiling away the bathing solution may have the effect of setting the deposits on the lenses, forming salt crystals within the lenses or, most seriously, heating the lenses to a temperature whereat their optical properties are lost or altered.

To avoid such risks to expensive contact lenses, cases have been developed wherein the contact lenses are sealed with a contact lens bathing solution, and associated heating units have been developed to heat such a contact lens case and the solution therein to a temperature close to but preferably not to the boiling temperature of the solution, so that the lenses may be bathed in heated solution for substantial periods of time, i.e., overnight, without the risks associated with evaporation of the solution.

Such units are commonly heated with electrical heating elements which are thermostatically controlled to heat the case containing the contact lens bathing solution to the desired temperature. Conceptually, such units should provide for long-term trouble-free use. Due to misuse or carelessness, however, such has not been the case. The task of bathing contact lenses is a daily task which becomes routine and is not always carefully attended to. Sometimes, a case, which contains a pair of contact lenses, is improperly closed, causing the contact lens solution to spill out. In addition to risks to the lenses caused by loss of bathing solution, an electrolytic bathing solution spilling on the heating unit may cause shorting of the heating unit and associated electrical damage. Shorting of the heating unit may have various consequences. For example, shorting of the thermostat may lead to overheating, evaporation of the solution, and destruction of the lenses.

It is an object of the present invention to provide a new and improved contact lens heating unit which substantially overcomes the shortcomings above-described.

It is a further object of the invention to alert a contact lens user when a contact lens bathing case is improperly closed.

These and other objects of the invention will be more readily apparent from the following description of the drawings in which:

FIG. 1 is a perspective view of an open heating unit containing a contact lens bathing case;

FIG. 2 is a perspective view of a closure member and a container member of the contact lens bathing case;

FIG. 3 is an elevation view of the lower side of the closure member illustrated in FIG. 2;

FIG. 4 is a cross-sectional view of the closed heating unit containing a bathing case;

FIG. 6 is an exploded view of the contact lens bathing case heating unit of FIG. 1;

FIG. 7a is a plan view of the bathing case holder;

FIG. 7b is an elevation view of the bathing case holder;

FIG. 8 is a cross-sectional view of the lower portions of the heating unit;

FIG. 10 is a cross-sectional view, similar to that of FIG. 5, in which the bathing case holder is located between its open and closed positions;

FIG. 12 is a cross-sectional view similar to that of FIG. 9 showing an attempt to close the heating unit when the bathing case is closed to the extent shown in FIG. 11;

FIG. 13 is a view similar to that of FIG. 10 in which a very loosely closed bathing case is inserted in the bathing case holder and showing an abortive attempt to close the heating unit; and FIG. 14 is a further view similar to that of FIG. 5 in which an improperly closed bathing case is inserted into the bathing case holder and showing an abortive attempt to close the heating unit.

Figure 5:
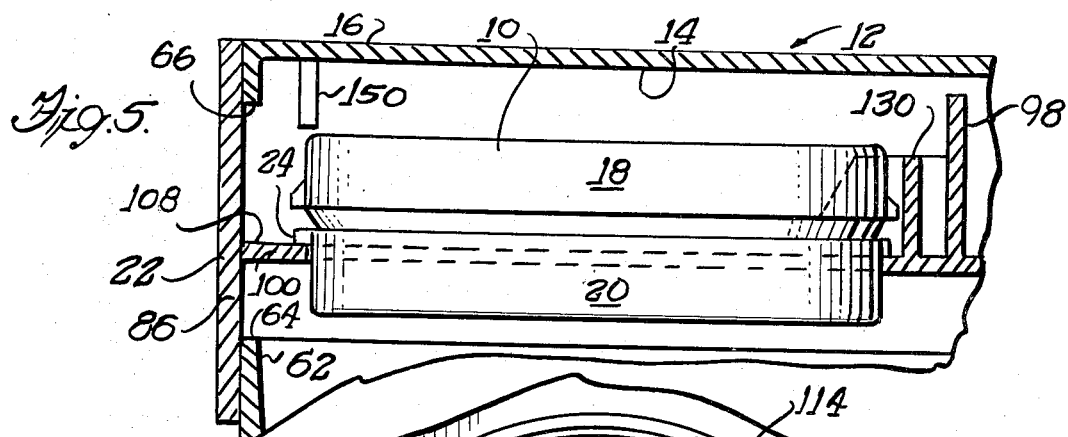
FIG. 5 is a cross-sectional view of the closed bathing case compartment of the heating unit and containing the contact lens bathing case.

In accordance with the present invention, the solution leakage problem due to improper closure of the lens case 10 is overcome by requiring the lens case to be properly closed before it can be placed in proper position adjacent the heating unit 12 and within a closed compartment 14 (FIG. 4) in the housing 16. This is achieved by means on upper and lower portions 18 and 20 (FIG. 2) of the lens cleaning case 10 which are properly positioned relative to a holder 22 in the compartment 14 such that the lens case 10 will not fit within the compartment when the compartment is closed unless the upper and lower portions are tightly engaged to prevent leakage of the solution during subsequent heating. In the preferred embodiment of the invention, lug means 24 (FIG. 2) are provided on the lens case 10 for positioning relative to each other when the lens case is properly closed, and the lug means cooperate with portions of the compartment 14 such that the compartment cannot be closed if the lug means are not properly positioned due to improper closure of the upper and lower portions of the lens case.

In accordance with an important aspect of the invention, the lens case 10 is carried by the slidable holder 22 (FIG. 1), which is movable from an open position spaced away from the heating means for receiving the lens case, to a closed position interiorly of the housing 16 at a location adjacent the heating means whereby the solution and lens may be heated while within the lens case.

The contact lens bathing case 10 (FIG. 2) is comprised of the lower portion or container member 20 and the upper portion or closure member 18 which is rotatably applied to the container member 20. The container member 20 has a circular bottom 26 and a cylindrical skirt 28 extending upward therefrom. Likewise, the closure member 18 has a circular top 30 and a cylindrical skirt 32 depending downward therefrom. The skirt 32 of the closure member 18 has a greater diameter than the skirt 28 of the container member 20 so that thread 34 on an upper portion of the outer wall of the container member skirt 28 cooperates with thread 36 on a lower portion of the interior wall of the closure member skirt 32 to close the case 10. An annular resilient sealing ring 38 (FIG. 3) is provided around the edge of the lower surface of the top 30 of the closure member 18. When the closure member 18 is fully applied to the container member 20, an upper edge 40 (FIG. 2) of the container member skirt 28 abuts the resilient sealing ring 38 for sealing the bathing solution within the case 10.

For the purpose of holding the contact lens within the bathing case 10, the latter is provided, as seen in FIG. 3, with a contact lens retainer assembly 42 which depends from the top 30 of the closure member 18 to hold the contact lenses in the solution when the closure member is applied to the filled container member 20. With the closure member 18 inverted and laid flat on its top 30, the concave back side of the lens is laid on a cooperating convex surface 44. A hinged retainer 46 is snapped into locking position with a latch 48 so that each retainer holds a contact lens between it and the convex surface 44. The retainer 46 includes an annular ring 50, with an open center 52. The ring 50 is of appropriate diameter to hold the periphery of the lens, and the open center 52 has a sufficient diameter to permit unobstructed contact between the optical center of the lens and the solution. The locked retainer 46 is sufficiently spaced from the convex surface 44 so that the lens is loosely located therebetween to permit the solution to bathe the concave surface of the lens.

The housing 16 of the heating unit 12 into which the bathing case 14 is inserted has an upper portion 56 (FIG. 1) generally in the shape of a rectangular box with rounded edges for aesthetic purposes. A lower base portion 58 is recessed from each side 57 of the upper portion 56 providing shoulders 60 extending the length of the heating unit 12.

To provide a slot 68 in one of the housing 16 through which the slidable holder 22 travels, a flat lower front panel 62 (FIG. 6) of the housing has a horizontal upper edge 64 spaced apart from an upper front rim 66 of the housing.

The heating means, which comprises a heating element 70 (FIG. 4) and a thermostat (not shown) to control the temperature, lies generally flat along the bottom of the heating unit base section 58. A recess 76 in the back of the heating unit 12 and electrical prongs 78 extending through a vertical back panel 80 of the recess 76 form an electrical plug 74 to connect the heating element 70 to an outside power line. A light 82, extending upward of the top of the housing 16 indicates that the unit 12 is plugged in and heating.

The case holder 22 functions as a drawer or slide which is slidably disposed in the housing 16 and which is (as best seen in FIG. 4) horizontally displaceable from a closed position adjacent to the heating element 70 to an open position remote from the heating element to receive the case 10. The front 86 of the holder 22 is a flat vertically disposed panel with size and shape to match and to close the upper portion 56 of the housing 16, so that when the holder is located in its closed position, the front 86 of the holder locates flush against the front of the housing.

Means are provided to guide the case holder 22 for sliding travel in the housing 16 and to this end, a pair of guides 90 extend behind the front 86 of the holder 22 a distance generally equal to the length of the housing. A pair of parallel spaced guide slots 92 (FIG. 6) extend through the front panel 62 of the housing 16 and substantially along the length of the shoulders 60 to receive the guides 90 therein. The bottom edge 94 of each guide 90 slides against the bottom 96 of the corresponding guide slot 92 as the holder 22 is displaced between its open and closed position.

To receive and hold a lens case 10 for travel, the holder 22 is provided with a horizontal holder panel 100 which extends from the front panel 86 and along the upper edges of the guides 90 to a point generally midway between the front panel 86 and the back of the guides. The guides 90 are proportioned so that, as the lower edge 94 of the guides slide along the lower surface 96 of the guide slots 92, the lower surface 102 of the horizontal panel 100 is positioned above the front edge 64 of the housing 16. A back holder panel 98 extends vertically from the back edge of the horizontal holder panel 100 and, in the closed position of the holder 22, is positioned directly in front of a vertically disposed housing center panel 99 depending from the top 84 of the housing 16.

To guide the holder 22 for sliding movement and to prevent lifting of guides 90 from their guide slots 92 in the housing 16, the latter is formed with a plurality of positioning flanges 104 (FIG. 4) which extend inward of the sides 57 of the housing 16 and have horizontal bottom edges 105 which position the upper surface 108 of the horizontal holder panel 100 and the upper surfaces 109 of the guides 90 therebelow. Furthermore, the bottom edges 105 of the positioning flanges 104 cooperate with the upper surfaces 109 of the guides 90 to prevent the extended portion of the holder 22 from tipping downward when the holder 22 is extended to its open position with its center of gravity exterior of the housing 16.

To receive and hold the lens case 10 in its travel toward and from the heating unit 70, a case locating means is associated with the holder 22, and it comprises a well 110 (FIGS. 7a and 7b) into which the closed bathing lens case 10 is inserted. The well 110 comprises an opening 112 in the horizontal holder panel 100 of slightly greater diameter than the exterior diameter of the container member 20, to receive the container member therein, and an annular rib or lip 114 extending upward from the edge the opening.

To assure proper positioning of a properly closed lens case 10 in the well 110, the lug means 24 on the lens case must be received in a pair of opposed grooves or slots formed in the annular rib 114. More specifically, the rib 114 includes a pair of inner lip portions 116, which have a uniformly low height, and an insertion prevention outer lip portion 118. The interior diameter of the inner lip portions 116 is slightly greater than the exterior diameter of the container member 20 but less than the exterior diameter of the closure member 18, so that the lower edge of the closure member skirt 32 rests on the upper edges 122 of the inner lip portions 116 when the container member 20 of a closed case 10 is inserted within the inner lip portions. The front ends 124a and back ends 124b of the inner lip portions 116 are spaced apart to provide front and back slots 126a and 126b therebetween which extend down to the upper surface 108 of the horizontal holder panel 100. The outer lip portion 118 comprises edge sections 128 which extend upward of the back of the upper edges 116 of the inner lip portions 116 and a joining center section 130. The edge sections 128, which increase in height from their front ends to the greater height of the center section 130, have an arcuate interior wall 132 slightly greater than the exterior diameter of the closure member 18. A pair of vertical shoulders 133 join the center section 130 to the edge sections 122 of the outer lip portion 118 and space the interior wall 134 of the center section 130 away from the edge of the well opening 112. The interior wall 134 of the center section 130 and the shoulders 133 extend the back vertical slot 126b above the lower lip portions 116.

The lug means 24 on the lens case 10 for insertion into the receiving slots 126a and 126b on the lip 114 comprises a pair of alignment lugs 140 which extend outward of the container member 20 at opposite ends of a diameter thereof and locate in the slots 126a and 126b between the ends 124a and 124b of the inner lip portions 116. The lower surfaces of the alignment lugs 142 rest on the upper surface 108 of the horizontal panel 100 and are vertically positioned on the container member wall to hold the lower end 26 of the container member 20 above the upper edge 64 of the housing front panel 62 and permit displacement of the case-carrying holder 22 between its open and closed positions.

Figure 9:
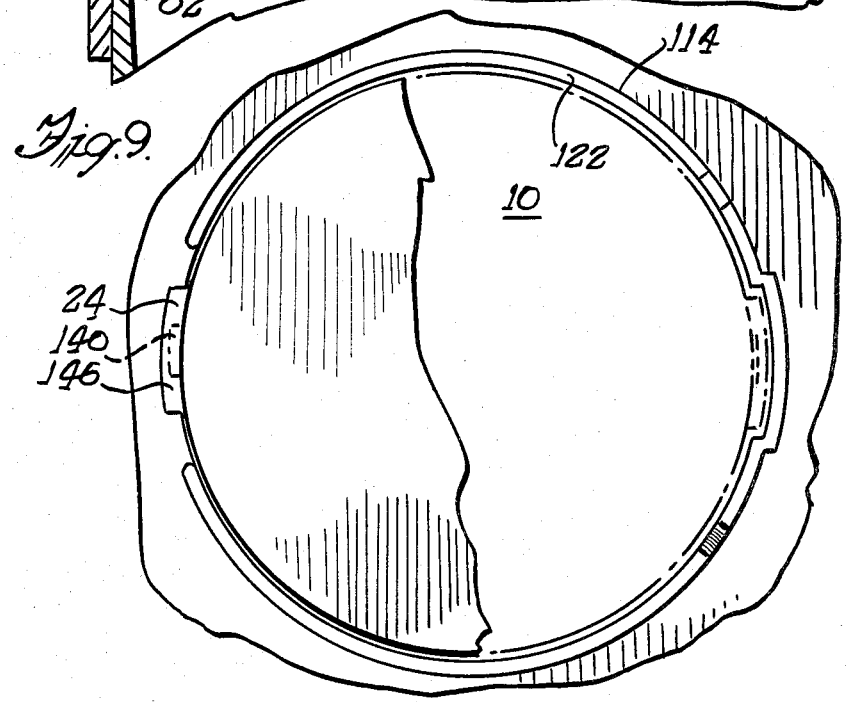
FIG. 9 is a plan view of a contact lens bathing case inserted in the case holder.

A pair of insertion prevention lugs 146, which extend outward of the closure member 18 at each end of a diameter thereof, have a radius as measured from the center of the closure member which exceeds that of the interior arcuate walls 132 of the edge sections 128 of the outer lip portion 118 but which is less than that of the interior wall 134 of the central portion 130 to permit one of the closure member lugs 146 to locate within the upper extension of the back vertical slot 126b. When the closure member 18 is properly threaded and in sealed relationship to the container member 20, the closure member lugs 146 are aligned with the container member lugs 140 (FIG. 9). When the properly closed case 10 is inserted in the well 110 (FIG. 5) so that the alignment lugs 140 of the container member 20 locate on the horizontal holder panel 100, one of the closure member lugs 146 locates in the upper extension of the back vertical slot 126b and permits full insertion of the case into the well.

It should be noted that the use of two container member lugs 140 and two closure member lugs 146 is occasioned by the case 10 having two closed positions of the closure member 18 relative to the container member 20 due to the thread design. Modifications particular to bathing cases having other numbers of closed positions would have a number of lugs on each member corresponding to each closed position.

Closure prevention means in the form of a pair of stops 150 (FIGS. 4 and 12) depend from the top 84 of the housing 16 toward the front end thereof and are spaced from the horizontal holder panel 108 a distance which provides minimal clearance for the bathing case 10 during closing of the heating unit 12 when the bathing case 10 is fully closed and fully inserted in the well 110. However, if the closure member 18 is improperly applied to the container member 20 or if the case 10 is improperly inserted in the well 110, the case 10 abuts the stops 150 during closing of the heating unit 12 so that the holder 22 may not be displaced to its closed position. The stops 150 also abut the front of the back holder 22 panel 98 to prevent the holder from being removed completely from the housing 16.

Illustrated in FIGS. 9 and 10 is a case 10 in which the closure member 18 is fully applied to the container member 20 and is fully inserted into the well 110 with a container member lug 140 and an aligned closure member lug 146 located in the back vertical slot 126b. The top 30 of the fully closed and correctly inserted case 10 passes below the stops 150 depending from the top 84 of the housing 16 to permit horizontal displacement of the holder 22 to its closed position within the heating unit 12.

Figure 11:
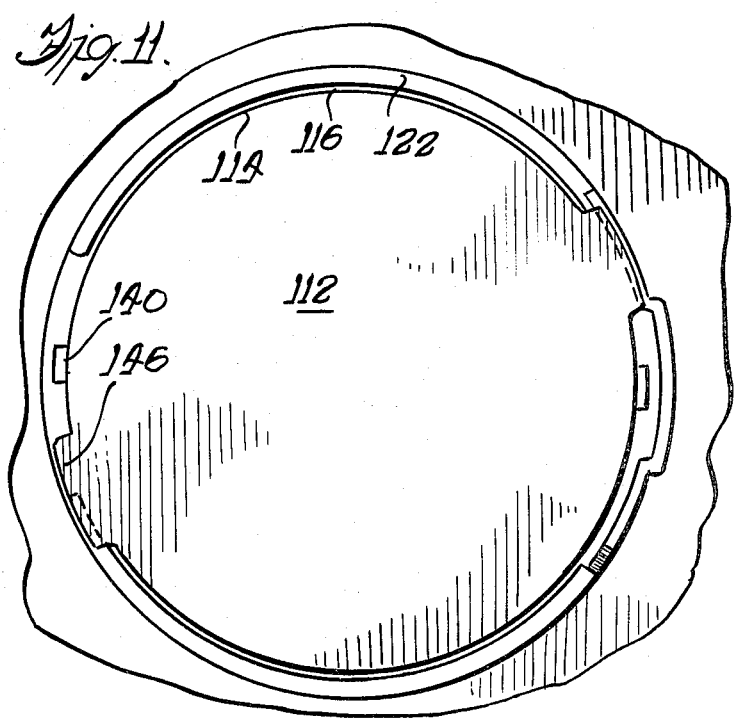
FIG. 11 is a top plan view of a bathing case which is not completely tightened and which is partially inserted into the bathing case holder.

Illustrated in FIG. 11 is a case 10 wherein the closure member 18 is applied to the container member 20 but rotated to a position just short of fully closed. The case 10 is inserted so that the container member alignment lugs 140 locate in the slots 126a and 126b between the spaced ends 124a and 124b of the lower lip portions 16, but the corresponding misaligned container member lug 146 rests on the upper edge of the outer lip portion 118 and prevents the container member 20 from being fully inserted into the well 110. As seen in corresponding FIG. 12, the partially inserted case 10 abuts the stops 150 and thus aborts an attempt to close the heating unit 12 and alerts the user that the case is improperly closed.

In FIG. 13 the closure member 18 is correctly but loosely applied to the container member 20 so that the closure member position is about 90° from fully closing the case 10. The container member lugs 140 locate in the vertical slots 126a and 126b and and the closure member lugs 146 are sufficiently displaced therefrom so as not to contact the outer lip portion 118 and prevent full insertion of the container member 20 into the well 110. However, the incomplete closing of the case 10 gives the bathing case added height so that the case does not pass through the minimal clearance beneath the stops 150.

Illustrated in FIG. 14 is a case 10 in which the closure member 18 is improperly applied to the container member 20 so that the threads do not cooperate. Nevertheless the closure member 18 is forcibly applied to the container member 20 so that the lugs 140 and 146 align and locate within the vertical slots 126a and 126b. The elevated side of the case 10, resulting from the misapplication of the closure member 18, will not pass below the stops 150 and, indeed, as illustrated, does not pass below the upper front rim 66 of the housing 16.

While the invention has been described in terms of a preferred embodiment, modifications obvious to one skilled in the art may be made without departing from the scope of the present invention. For example, a simplified version of the heating unit could provide a slidable holder with a flat holder panel, having no well, on which a case is placed. Means to prevent closure of an improperly applied case could consist solely of closure prevention means in the form of stops which allow a minimal clearance therebelow so that the added height of an improperly closed case causes the case to abut the stops and prevent closing of the heating unit.

Alternatively, the case holder could consist of a compartment with a latched top which swings away to an open position for receiving the bathing case. The added height of an improperly closed case could prevent the cover from being swung to a fully closed position. The slideable type holder herein described, however, is preferred because any spilled fluid resulting from an improperly closed case takes place remote from the heating element. A slideable type holder is also preferred to a unit with hinged cover, because direct access to the heating element is prevented, and because failure to close the drawer will prevent the case from being located adjacent to the heating element. While with a hinged cover unit, a user may have access to the heating element or may be tempted to ignore the fact that the unit is only partially closed.

The scope of the invention is limited only by the following claims.

What is claimed is:

1. Apparatus for heating contact lenses comprising
a removable lens case composed of a container member for receiving contact lens treating solutions and a closure member for said container member, said container member having an alignment means, said closure member having an insertion prevention means,
a housing defining a compartment for said lens case,
heating means within said housing adjacent said compartment,
a holder for said lens case adapted to be received within said compartment, said holder having case locating means which cooperate with said alignment means to permit placement of said lens case in said holder only in a predetermined orientation, and
interference means which interfere with said insertion prevention means when said closure member is improperly applied to said container member to prevent the lens case from being fully inserted into said compartment.

2. Apparatus according to claim 1 wherein means provide a fluid-tight seal between said closure member and said container member when said closure member is properly applied to said container member.

3. Apparatus according to claim 1 including a cover member for enclosing said compartment when said lens case is fully inserted into said compartment.

4. Apparatus according to claim 1 wherein said holder has a vertical slot that provides said locating means and said interference means, said alignment means is a lug extending from said container member and insertable into said slot, and said insertion prevention means is a lug extending from said closure member insertable into said slot when aligned with said container member lug.

* * * * *